United States Patent [19]

Decnop et al.

[11] Patent Number: 5,149,840

[45] Date of Patent: Sep. 22, 1992

[54] HYDROXY FURANONE PREPARATION

[75] Inventors: Coenraad Decnop, Bussum; Johannes M. van Dort, Lage Vuursche; Johannes T. de Hey, Hilversum, all of Netherlands

[73] Assignee: Unilever Patent Holdings B.V., Rotterdam, Netherlands

[21] Appl. No.: 527,282

[22] Filed: May 18, 1990

[30] Foreign Application Priority Data

May 18, 1989 [EP] European Pat. Off. ........ 89201269.1

[51] Int. Cl.⁵ .......................................... C07D 307/58
[52] U.S. Cl. .................................................... 549/477
[58] Field of Search ................................ 549/313, 477

[56] References Cited

U.S. PATENT DOCUMENTS

| | | | |
|---|---|---|---|
| 2,936,308 | 5/1960 | Hodge | 536/22 |
| 3,455,702 | 7/1969 | Willham et al. | 549/477 |
| 3,558,664 | 1/1971 | Robinson et al. | 549/477 |
| 3,629,293 | 12/1971 | Peer et al. | 549/477 |
| 3,647,825 | 3/1972 | Shimizaki et al. | 549/477 |
| 4,013,800 | 3/1972 | Shimazaki et al. | 426/536 |
| 4,045,587 | 8/1977 | Katz et al. | 549/477 |
| 4,181,666 | 1/1980 | Huber et al. | 549/477 |
| 4,208,338 | 6/1980 | Huber et al. | 549/477 |
| 4,480,111 | 10/1984 | Whitesides et al. | 549/477 |

FOREIGN PATENT DOCUMENTS

| | | |
|---|---|---|
| 1132600 | 11/1968 | European Pat. Off. |
| 1238942 | 7/1971 | European Pat. Off. |
| A63-307869 | 1/1198 | Japan |
| 3307869 | 12/1988 | Japan |
| 1199101 | 7/1970 | United Kingdom |

OTHER PUBLICATIONS

Doornbos, Amadori Compounds, Derived from 6-Deoxy Sugars, as Flavour Precursors, Procceding of the International Symposium "Maillard Reactions in Food-Chemical, Physical and Technological Aspects", Uddevalla, Sweden Sep. 2-6, 1979.
Peer, "Degradation of Sugars and Their Reactions with Amino Acids", Misc. Papers, Landbouwhogeschool Wageningen No. 9, (1971) pp. 105–115.
H. Shigematsu, "Components of roasting flavor formed in the heating reaction between amino compounds and sugars", Chemical Abstracts, Jan. 2, 1978, p. 619, vol. 88, No. 1.
De Rijke et al. "Shigematsu variation of the Maillard reaction", Chemical Abstracts, May 10, 1982, p. 604 vol. 96, No. 19.
Doornbos et al., "Amadori compounds derived from 6-deoxy sugars, as flavor precursors", Chemical Abstracts, vol. 96, No. 11, Mar. 15, 1982, p. 488.
Shaw et al., "Hexose-amino acid degradation studies involving formation of pyrroles, furans, and other low molecular weight products", Journal of Agricultural and Food Chemistry, vol. 25, No. 3, May–Jun. 1977, pp. 641–644.
Heibl et al., "Isolation of 4-hydroxy-2-(hydroxymethyl)-5-methyl-3(2H)-furanone from sugar amino acid reaction mixture", Journal of Agricultural and Food Chemistry, vol. 35, No. 6, Nov.–Dec. 1987, pp. 990–993.
Peer et al., "The reaction of aldopentoses and secondary amine salts, a convenient . . .", Recueil, vol. 87, (1968), pp. 1011–1017.

*Primary Examiner*—C. Warren Ivy
*Assistant Examiner*—Amelia A. Owens
*Attorney, Agent, or Firm*—Cushman, Darby & Cushman

[57] ABSTRACT

The invention provides a process for the preparation of natural 5-methyl- and 2,5-dimethyl-4-hydroxy-2,3-dihydrofuran-3-one, by heating and reacting a pentose or 6-deoxyhexose in the presence of an amino acid and directly separating, the hydroxyfuranone from the reaction mixture by distillation under reduced pressure. Preferably the distillation is carried out in the presence of a high boiling organic solvent, particularly propylene glycol and glycerol. The amino acid is preferably lysine, proline or hydroxyproline.

9 Claims, No Drawings

HYDROXY FURANONE PREPARATION

The invention relates to an improved process for the preparation of 5-methyl- and 2,5-dimethyl-4-hydroxy-2,3-dihydrofuran-3-one.

These compounds are well known flavour components and are in great demand in the flavour and food industry, especially when prepared from natural starting materials.

Several methods of preparation of these compounds involving a pentose or a 6-deoxyhexose are known: U.S. Pat. No. 2,936,308 (Hodge) discloses the reaction of L-rhamnose and piperidine acetate at 75°C. for 18 hours in ethanol and a 26% yield of 2,5-dimethyl-4-hydroxy-2,3-dihydrofuran-3-one was obtained according to Example 2. Although the desired compound was formed in a reasonable yield, it was contaminated with a nitrogen-containing by-product (2,5-dimethyl-4-piperidino-2,3-dihydrofuran3one), which was difficult to remove. The same preparation is disclosed in GB 1,132,600. GB 1,238,942 discloses the reaction between a pentose or 6-deoxy-aldohexose with a dialkylamine to a glycosylamine which further reacts with acid to form the desired compounds. Before isolating the product from the reaction mixture the solvent is removed by distillation under reduced pressure at a temperature below 35° C. The product is then isolated through extraction with an organic solvent followed by purification through column chromatography.

These prior art processes are laborious and the products obtained are rather unstable and not natural. Reactions of sugars with amino acids (Maillard reactions) are known to produce complicated reaction mixtures including varying amounts of hydroxyfuranones, compare: H.G. Peer, Misc. Papers, Landbouwhogeschool Wageningen no. 9 (1971) and W. Baltes, Lebensmittelchemie u. gerichtl. Chemie 34 39-47 (1980). T. Doornbos et al., Proc. Int. Symp. Maillard Reaction in Food, Uddevalla, Sweden, Sept. 2-6, 1979, report that Amadori rearrangement products of 6-deoxyhexoses and several amino acids yield mixtures of products including 2,5-dimethyl-4-hydroxy-2,3-dihydro-furan-3-one. However no simple ways have heretofore been disclosed to isolate the reputedly unstable hydroxyfuranones from these complicated reaction mixtures.

It has now been found that 5-methyl- and 2,5-dimethyl-4-hydroxy-2,3-dihydrofuran-3-one of high purity and stability can be prepared in a process involving reacting a pentose or 6-deoxy-hexose in the presence of an amino acid, and directly separating the hydroxyfuranone from the reaction mixture, preferably by distillation under reduced pressure. When the starting materials are derived from natural sources, the end product obtained can be referred to as a natural product.

The 6-deoxyhexose employed in the process according to the present invention is preferably rhamnose, in particular L-rhamnose, but also other 6-deoxyhexoses like fucose and quinovose (6) deoxyglucos can be employed. In order to obtain a natural hydroxyfuranone according to the present invention it is necessary to use a natural and preferably a pure 6-deoxyhexose starting material, and recrystallized material is preferred. It is recommendable that the 6-deoxyhexose has a low content (below 1%) of hexoses, in particular glucose, as such impurities may lead to lower yields of hydroxyfuranone.

Special techniques are available for preparing natural and pure 6-deoxyhexose from suitable, naturally occurring glycosides as e.g. naringin, rutin, quercitrin, fenugreek, gum arabic, gum acacia (such as kordofan, talha), neohesperidin, microbial rhamnolipids, and microbial rhamnopolysaccharides (e.g. polyrhamnose).

The pentose employed in the synthesis according to the present invention is preferably xylose. This material should likewise be of natural origin to obtain a natural -methyl-hydroxy-dihydrofuranone. Pure, recrystallized material is preferred.

The amino acids preferably used in the method according to the present invention are lysine, proline and hydroxy-proline or mixtures of thereof. The amino acid preferably is a pure, food grade and natural material.

The distillation of the product from the reaction mixture is preferably carried out in the presence of a high boiling organic solvent yielding a solution of the hydroxyfuranone in that solvent. The product may be separated from this solution through cooling followed by filtration of the crystallized hydroxyfuranone from the solvent. The filtrate can be recycled in the next distillation and thus the loss of product still present in the filtrate is prevented. Alternatively, the hydroxyfuranone solution may also be used as such as a flavour component, with or without any further concentration.

Especially suitable solvents are those from which the hydroxy-furanone crystallizes on cooling of the distillate and which have a boiling point within 50° C. from the boiling point of the hydroxyfuranone at the distillation pressure. This pressure is preferably chosen below 5 kPa (37 mm Hg) and more specifically below 2,5 kPa. Preferred solvents are those which are permitted for use in flavourings by the relevant food regulations. Examples of such suitable solvents are propylene glycol, glycerol and xylitol. If a non-permitted solvent is used, the hydroxy-furanone has to be separated from the solvent and traces of solvent adhering to the crystalline hydroxyfuranone may be removed by washing with a small and cooled quantity of a permitted solvent, such as ethanol.

The process may be carried out by either reacting pentose or 6-deoxyhexose with amino acid without any added reaction medium, or preferably by reacting them in a suitable reaction medium, such as water, ethanol or a high boiling solvent. Preferred high boiling solvents are those which are also used during the distillation. If water is used as the reaction medium it is usually an aqueous buffer solution with a pH value between 4.0 and 8.0, preferably between 5.0 and 8.0.

The presence of phosphate ions in the reaction medium is often beneficial for the reaction. Dilute phosphate buffer solution is therefore preferred as an aqueous medium. Acetate or citrate buffer solutions may also be employed.

The reaction temperature will generally be between 50° C. and 180° C., depending on the reaction medium used; in an aqueous medium it is preferably between 60° and 100° C. The reaction period depends on the temperature and will generally be between 30 minutes and 5 days, preferably between 30 minutes and 20 hours, more preferably between 45 minutes and 5 hours. Molar ratios of pentose or 6-deoxyhexose to amino acid between 1:10 and 20:1 are suitable. Preferably the ratio is between 1:1 and 15:1. Particularly preferred is a 1.25-10 fold molar excess of pentose or deoxyhexose.

If the high-boiling solvent used for the distillation is not used as the reaction medium, it may be added at any time during or after the reaction, but before the distillation is started. It may be advantageous to add extra high boiling solvent during the distillation, preferably in small quantities to prevent a sudden drop of temperature in the distillation pot. Alternatively, the reaction mixture may be added gradually to a quantity of boiling solvent while distilling.

The purity of the hydroxyfuranones obtained by the process according to the invention is generally excellent so further purification is superfluous in most cases. The storage stability of the products was found to be good, especially when stored in a nitrogen atmosphere, under conditions where the usual commercial grades show decomposition.

The hydroxyfuranones thus obtained are valuable ingredients for various flavour (fruit, meat, savoury and bakery notes) and for certain perfumery applications.

EXAMPLE 1

| Starting materials | g |
| --- | --- |
| L-lysine (of natural origin) | 38 |
| Sodium dihydrogen orthophosphate.2H$_2$O | 260 |
| Water | 410 |
| L-rhamnose monohydrate (of natural origin) | 600 |
| Sodium hydroxide (solid) | 51 |

Procedure

All of the solids, except the rhamnose, were added to the water and the mixture was stirred and heated to 70° C. until complete dissolution. Then the rhamnose was added. The resulting solution was further heated and maintained at 100° C. for 3 hours. After cooling to room temperature the reaction mixture separated into two layers which were separated and each analysed for their 2,5-dimethyl-4-hydroxy-2,3-dihydrofuran-3-one content. The lower layer contained a negligible amount of this compound and was discarded. To the upper layer, which contained 196 g of the hydroxy-furanone, was added 200 g of propylene glycol. This mixture was subsequently distilled under reduced pressure. The distillation temperature gradually rose to 69° C. and the pressure dropped to 3.5 kPa while the distillate consisted of a mixture of water and propylene glycol. Thereafter the pressure dropped to below 0.2 kPa and a fraction was collected weighing 42 g and containing 12% w/w of the hydroxyfuranone. The distillation temperature further rose to 75° C. and finally to 79° C. while 2 fractions were collected consisting of about equal amounts of propylene glycol and 2,5-dimethyl-4-hydroxy-2,3-dihydrofuran-3-one and weighing 223 and 131 g respectively. During the collection of the first of these two fractions another 50 g of propylene glycol was gradually added to the boiling mixture. These two fractions were combined and after inoculation with a few crystals of hydroxyfuranone cooled to 5° C. When crystallization was complete the crystals were collected by suction filtration and washed with ice-cold propylene glycol. The yield of dry crystals was 160 g, giving a direct yield of 38% on rhamnose. The propylene glycol filtrate, which still contained some hydroxyfuranone, was reused for the next preparation.

EXAMPLE 2

The procedure described in Example 1 was repeated, but the deoxyhexose used was L-fucose. In this case the yield of 2,5-dimethyl-4-hydroxy-2,3-dihydrofuran-3-one in the reaction mixture was 61% of theory.

EXAMPLE 3

The procedure described in Example 1 was followed, but the amino acid employed was L-hydroxyproline. In this case the yield of 2,5-dimethyl-4-hydroxy-2,3-dihydrofuran-3-one in the reaction mixture was 63%

EXAMPLE 4

| Starting materials | g |
| --- | --- |
| L-proline (of natural origin) | 22.8 |
| L-rhamnose monohydrate (of natural origin) | 145.6 |
| Propylene glycol | 200.0 |

Procedure

While stirring under nitrogen, the mixture of starting materials is heated to 80° C. and kept at this temperature for 2½ hours. Subsequently, the mixture is distilled under reduced pressure yielding 192 g propylene glycol, bpt.: 70°–80° C., while the temperature of the distillation flask is kept below 115° C. Then the temperature of the distillation flask is gradualy raised to 130°–140° C. and 60 g of a mixture containing propylene glycol and 2,5-dimethyl-4-hydroxy-2,3-dihydrofuran-3one (63% w/w = 37.8 g) is collected. To the end of the distillation the temperature is raised to 170° C. and the pressure drops to 0.7 kPa. After inoculation with a few crystals of hydroxyfuranone, the distillate was cooled to 5° C. When crystallization was complete the crystals were collected by suction filtration and washed with ice-cold propylene glycol. The yield of dry crystals was 31 g, giving a direct yield of 30.3% on rhamnose. The propylene glycol filtrate, which still contained some hydroxyfuranone, was reused for the next preparation. Thus a total yield of 37% of theory was reached.

EXAMPLE 5

The procedure of Example 4 was repeated using 200 g glycerol instead of propylene glycol. A direct yield of 25% of dry crystals was obtained. The filtrate was reused for the next preparation, giving an overal yield of 35% of theory.

EXAMPLE 6

| Starting materials | g |
| --- | --- |
| L-proline (of natural origin) | 1.6 |
| Sodium dihydrogen orthophosphate. 2H$_2$O | 12.0 |
| Potassium orthophosphate. 3H$_2$O | 3.7 |
| Xylose | 8.4 |
| Glycerol | 85.0 |

Procedure

While stirring under nitrogen, the mixture of starting materials is heated to 65° C. and kept at this temperature for 7 hours. Subsequently, the mixture is distilled at a pressure of 2 Pa and a temperature of 150° C. using a short path distillation apparatus (Leybold Heraeus, type KWD1). 80 g of a 0.8% solution of 5-methyl-4-hydroxy-2,3-dihydrofuran-3-one in glycerol was obtained, representing a yield of 10 % of theory.

We claim:

1. Process for preparation of 5-methyl- or 2,5-dimethyl-4-hydroxy-2,3-dihydrofuran-3-one comprising the steps of:
a reacting a pentose or 6-deoxyhexose in the presence of an amino acid:
  i at a temperature between 50° and 180° C.,
  ii for a time between 30 min. and 5 days,
  iii in a molar ration of sugar:amino acid of between 1:10 and 20:1,
b distilling the hydroxyfuranone from the reaction mixture at a pressure below 5 kPa and in the presence of an organic solvent having a boiling point within 50° C. of that of the hydroxyfuranone at distillation pressure.

2. Process according to claim 1 wherein the high boiling solvent is propylene gylcol, glycerol or xylitol.

3. Process according to claim 1 wherein the reaction is carried out in a reaction medium selected from the group consisting of water, ethanol and the organic solvent.

4. Process according to claim 3 wherein the reaction is carried out in an aqueous medium buffered to a pH value between 4.0 and 8.0.

5. Process according to claim 3 wherein the reaction medium contains phosphate and/or citrate ions.

6. Process according to claim 1 wherein the amino acid is lysine, proline, hydroxyproline or a mixture thereof.

7. Process according to claim 1 wherein the molar ratio of pentose or deoxyhexose to amino acid is between 1.25:1 end 10:1.

8. Process for the preparation of 5-methyl- or 2,5-dimethyl-4-hydroxy-2,3-dihydrofuran-3-one comprising the steps of:
a reacting a pentose or 6-deoxyhexose in the presence of an amino acid:
  i at a temperature between 50° and 180° C.,
  ii for a time between 30 min. and 20 hours,
  iii in a molar ratio of sugar:amino acid of between 1.25:1 and 10:1,
  iv in a reaction medium chosen from water, ethanol, propylene glycol, glycerol and xylitol,
  v wherein the amino acid is chosen from lysine, proline and hydroxyproline;
b distilling the hydroxyfuranone from the reaction mixture at a pressure below 5 kPa and in the presence of a solvent chosen from propylene glycol, glycerol and xylitol.

9. Process for the preparation of 5-methyl- or 2,5-dimethyl-4hydroxy-2,3-dihydrofuran-3-one comprising the steps of:
a reacting a pentose of 6-deoxyhexose in the presence of an amino acid:
  i at a temperature between 50° and 180° C.,
  ii for a time between 30 minutes and 5 days,
  iii in a molar ratio of sugar:amino acid of between 1:10 and 20:1,
b distilling the hydroxyfuranone from the reaction mixture at a pressure below 5 kPa and in the presence of an organic solvent having a boiling point within 50° C. of that of the hydroxyfuranone at distillation pressure,
wherein the organic solvent may be used in flavourings and the amino acid is lysine, proline, hydroxyproline or a mixture thereof.

* * * * *